US009814729B2

(12) United States Patent
Niquet et al.

(10) Patent No.: US 9,814,729 B2
(45) Date of Patent: Nov. 14, 2017

(54) NERVE AGENT ANTIDOTES

(71) Applicant: The Regents of the University of California, Oakland, CA (US)

(72) Inventors: Jerome Niquet, Irvine, CA (US); Claude G. Wasterlain, Granada Hills, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 459 days.

(21) Appl. No.: 13/830,615

(22) Filed: Mar. 14, 2013

(65) Prior Publication Data

US 2014/0249140 A1  Sep. 4, 2014

Related U.S. Application Data

(60) Provisional application No. 61/610,771, filed on Mar. 14, 2012.

(51) Int. Cl.
*A61K 31/5517* (2006.01)
*A61K 31/40* (2006.01)
*A61K 31/19* (2006.01)
*A61K 31/135* (2006.01)
*A61K 31/5513* (2006.01)
*A61K 45/06* (2006.01)
*A61K 31/20* (2006.01)
*A61K 31/4015* (2006.01)

(52) U.S. Cl.
CPC ........ *A61K 31/5513* (2013.01); *A61K 31/135* (2013.01); *A61K 31/20* (2013.01); *A61K 31/4015* (2013.01); *A61K 45/06* (2013.01)

(58) Field of Classification Search
CPC .... A61K 31/5513; A61K 45/06; A61K 31/20; A61K 31/4015; A61K 31/135; A61K 2300/00
See application file for complete search history.

(56) References Cited

PUBLICATIONS

Sushma Bhatnagar, Seema Mishra, Meenu Gupta, Madhurima Srikanti, Anindya Mondol, Alok Diwedi, Efficacy and safety of a mixture of ketamine, midazolam and atropine for procedural sedation in paediatric oncology: a randomised study of oral versus intramuscular route, Journal of Paediatrics and Child Health, vol. 44, Iss 4, p. 201-204, Apr. 2008.*
Harald Prüss, Martin Holtkamp, Ketamine successfully terminates malignant status epilepticus, Epilepsy Research (2008) 82, 219-222.*
James W Y Chen, Claude G Wasterlain, Status epilepticus: pathophysiology and management in Adults, Lancet Neurol 2006; 5: 246-56.*
Craig Lehmann, PharmD, and Gerald L. Wannarka, PhD, Bioavailability and Dose Proportionality of Intramuscular Diazepam Administered by Autoinjector, J Clin Pharmacol 2008;48:436-444.*
Claude G. Wasterlain, Roger Baldwin, David E. Naylor, Kerry W. Thompson, Lucie Suchomelova, and Jerome Niquet, Rational polytherapy in the treatment of acute seizures and status epilepticus, Epilepsia, 52(Suppl. 8):70-71, 2011.*
Jong Woo Lee and Barbara Dworetzky, Rational Polytherapy with Antiepileptic Drugs, Pharmaceuticals 2010, 3, 2362-2379.*
A Matagne, D-G Margineanu, B Kenda, P Michel and H Klitgaard, Anti-convulsive and anti-epileptic properties of brivaracetam (ucb 34714), a high-affinity ligand for the synaptic vesicle protein, SV2A, British Journal of Pharmacology (2008) 154, 1662-1671.*
Chen et al., "Status epilepticus: pathophysiology and management in adults," *Lancet Neurol*, 2006, 5:246-56.
Goodkin et al., "Subunit-Specific Trafficking of $GABA_A$ Receptors during Status Epilepticus," *The Journal of Neuroscience*, 2008, 28(10):2527-2538.
Lopez-Meraz et al., "Distinct caspase pathways mediate necrosis and apoptosis in subpopulations of hippocampal neurons after status epilepticus," *Epilepsia*, 2010, 51(Suppl. 3):56-60.
Mazarati et al., "Self-sustaining status epilepticus after brief electrical stimulation of the performant path," *Brain Research*, 1998, 801:251-253.
Mazarati et al., "Time-dependent decrease in the effectiveness of antiepileptic drugs during the course of self-sustaining status epilepticus," *Brain Research*, 1998, 814:179-185.
Mazarati et al., "Galanin Modulation of Seizures and Seizure Modulation of Hippocampal Galanin in Animal Models of Status Epilepticus," *The Journal of Neuroscience*, 1998, 18(23):10070-10077.
Naylor et al., "Synaptic NMDA receptor numbers increase in dentate gyrus granule cells during status epilepticus," *Neuroscience*, 2003, Abstract.
Naylor et al., "Trafficking of $GABA_A$ Receptors, Loss of Inhibition, and a Mechanism for Pharmacoresistance in Status Epilepticus," *The Journal of Neuroscience*, 2005, 25(34):7724-7733.
Naylor et al., "Rapid surface accumulation of NMDA receptors increases glutamatergic excitation during status epilepticus," *Neurobiology of Disease*, 2013, 54:225-238.
Suchomelova et al., "Treatment of Experimental Status Epilepticus in Immature Rats: Dissociation Between Anticonvulsant and Antiepileptogenic Effects," *Pediatric Research*, 2006, 59(2):237-243.
Tetz et al., "Development of a rat pilocarpine model of seizure/status epilepticus that mimics chemical warfare nerve agent exposure," *Toxicol Ind Health*, 2006, 22:255-266.

(Continued)

*Primary Examiner* — Sarah Pihonak
*Assistant Examiner* — Jason A Deck
(74) *Attorney, Agent, or Firm* — Riverside Law LLP

(57) ABSTRACT

The present invention includes compositions that are useful in treating, ameliorating, or preventing nerve agent poisoning. The present invention also includes methods of preventing, treating or ameliorating nerve agent poisoning in a subject in need thereof, the method comprising administering to the subject an effective amount of a composition of the invention. The present invention also includes methods of preventing, treating or ameliorating a seizure induced by a disease or disorder in a subject in need thereof, the method comprising administering to the subject an effective amount of a composition of the invention. The present invention also comprises a kit comprising compositions of the invention.

17 Claims, 6 Drawing Sheets

(56) References Cited

PUBLICATIONS

Treiman et al., "A Comparison of Four Treatments for Generalized Convulsive Status Epilepticus," *The New Englad Journal of Medicine*, 1998, pp. 792-798.

Wasterlain et al., "Abstracts: Plenary Session," *Annals of Neurology*, 2002, Supplement 1.

Wasterlain et al., "Molecular basis of self-sustaining seizures and pharmacoresistance during status epilepticus: The receptor trafficking hypothesis revisited," *Epilepsia*, 2009, 50(Suppl. 12):16-18.

* cited by examiner

NERVE AGENT ANTIDOTES

CROSS-REFERENCE TO RELATED APPLICATIONS

The present invention claims priority to U.S. Provisional Patent Application No. 61/610,771, filed Mar. 14, 2012, the entire disclosure of which is incorporated by reference herein as if being set forth herein in its entirety.

STATEMENT REGARDING FEDERALLY SPONSORED RESEARCH OR DEVELOPMENT

This invention was made with government support under grants NS13515 and NS05974 from the National Institute of Neurological Disorders and Stroke (NINDS). This work was supported by the U.S. Department of Veterns Affairs, and the Federal Government has certain rights in the invention.

BACKGROUND OF THE INVENTION

It is without question that nerve agents, such as sarin and other organophosphates, pose one of the most serious threats of attack to human populations, particularly from terrorist groups. This is due in part to the ease with which nerve agents can be synthesized, concealed and transported, and of course to their potential for resulting in mass casualties. Unfortunately, many countries and their military forces still stockpile these nerve agents.

Seizures are the most treatment-refractory complication of nerve agent intoxication, and were a prominent feature in the Tokyo subway attacks (Nozaki et al., 1995, Lancet 345:980-981). These seizures turn into uncontrolled status epilepticus (SE), refractory to treatment with antiepileptic drugs (Shih et al., 1999, J Biomed Sci 6:86-96) and cause severe brain damage (Shih et al., 1999, J Biomed Sci 6:86-96; McDonough, 2002, Military Psychol 14:93-119; Joosen et al., 2009, Neurotoxicology 30:72-80) and chronic epilepsy (Pernot et al., 2009, Neuroscience 162:1351-65; de Araujo Furtado et al., 2010, Epilepsia 51:1503-10).

Soldiers and civilians exposed to nerve agents are currently treated with antidote kits such as Mark I (Atropine sulfate and Pralidoxime) and CANA (Diazepam). When injected within minutes of nerve agent exposure, these two injections can prevent or reduce the seizures. However, once seizures start, they become quickly resistant to the treatments. The seizures generated by these organophosphates quickly become self-sustaining, independent of their original cholinergic trigger, and refractory to standard treatment (benzodiazepines), and represent an unresolved problem to this very serious military and terrorist threat.

In addition, routine status epilepticus encountered in hospital emergency rooms as a result of many causes, such as due to head trauma, epilepsy, infection, stroke, drug abuse or withdrawal, shares many features in common with SE triggered by nerve agents. It also tends to become self-sustaining, pharmacoresistant and independent of its original cause (Wasterlain, and Treiman, 2006, from Status Epilepticus: Mechanisms and management. MIT Press, Boston; Mazarati et al., 1998, Brain Res 814:179-185; Wasterlain et al., 2000, Epilepsia 41:134-143; Chen and Wasterlain, 2006, Lancet Neurology 5:246-256).

Monotherapy is widely accepted as the current best option for treatment of epilepsy, and controlled studies of the treatment of status epilepticus (SE) have shown lorazepam monotherapy to be as effective as any treatment tested (Treiman et al., 1998, New Engl. J. Med 339:792-798). However, the major reasons for preferring monotherapy in the treatment of chronic epilepsy, such as minimizing lifelong exposure to potentially toxic drugs, may not apply to SE, an acute, life-threatening event of limited duration. There is a paucity of experimental or clinical evidence supporting the superiority of monotherapy in the treatment of acute seizures and SE. There is also no consensus on the criteria which allow comparisons between the benefits and adverse effects of mono- and polytherapy.

Many animal models of SE have previously been developed (Wasterlain, 1974, Epilepsia 15:155-176; Wasterlain, 1976, Neurology 26:975-986; Fujikawa, et al., 1989, Amer J Physiol 256:C1160-C1167; Thompson, et al. 1997, Brain Research 100:1-4; Mazarati, et al., 1998, Brain Res 814: 179-185; Mazarati, et al., 1998, J. Neurosci 18:10070-10077; Mazarati, et al., 1998, Brain Res. 801:251-253; Suchomelova, et al., 2006, Ped. Res. 59:237-243), which have elucidated many of the mechanisms involved in the development of that condition (Wasterlain, et al., 1972, Brain Res 39:278-284; Dwyer, et al., 1980, J Neurochem 34:1639-1647; Wasterlain, et al., 1984, Proc Natl Acad Sci USA 81:1253-1257; Bronstein, et al., 1988, Neurochem Res 13:83-86; Wasterlain, et al., 1993, Epilepsia 34:S-37-S53; Wasterlain, et al. Neurochem Res 18:527-532; Mazarati, et al., 1998, Brain Res 814:179-185; Mazarati, et al., 1998, J. Neurosci 18:10070-10077; Mazarati, et al., 1998, Brain Res. 801:251-253; Liu, et al., 1999, Proc Natl Acad Sci 96:5286-5291; Wasterlain, et al., 2000, Epilepsia 41:134-143; Lopez-Meraz et al., 2010, Epilepsia 51:56-60). An experimental model of pharmacoresistance to benzodiazepines (the standard treatment for SE) during SE has previously been described (Mazarati, et al., 1998, Brain Res 814:179-185; Mazarati, et al., 1998, J. Neurosci 18:10070-10077; Mazarati, et al., 1998, Brain Res. 801:251-253). Several books on SE have been published (Delgado-Escueta, et al., 1983, from Status Epilepticus: Mechanisms of Brain Damage and Treatment, Raven Press, N.Y.; Wasterlain and Vert, 1990, from Neonatal Seizures. Raven Press, New York; Wasterlain, et al., 2006, from Status Epilepticus: Mechanisms and management. MIT Press, Boston).

Recent studies have shown that seizure-induced trafficking of synaptic GABAA and glutamate receptors causes both a failure of GABAergic inhibition and an increase in glutamatergic excitation during SE (Mazarati, et al., 1998, Brain Res 814:179-185; Mazarati, et al., 1998, J. Neurosci 18:10070-10077; Mazarati et al., 1998, Brain Res. 801:251-253; Naylor, et al., 2005, J Neurosci 25:7724-7733; Goodkin, et al., 2008, J Neurosci 28:2527-38; Wasterlain, et al., 2002, Ann. Neurol. 52(S1):516).

Recent work has demonstrated that during experimental SE in the rat, the initiation of self-sustaining seizures during SE and the development of pharmacoresistance to benzodiazepines result in part from the seizure-associated internalization of synaptic GABAA receptors in key brain regions (Naylor, et al., 2005, J Neurosci 25:7724-7733). The internalization of synaptic GABAA receptors results in temporary inactivation of those receptors, which decreases inhibition at a time when the brain needs it most and explains in part why seizures become self-sustaining. It also reduces the potency of drugs such as benzodiazepines, which act on those receptors. With fewer active synaptic receptors to bind to, the therapeutic effect of these drugs is significantly reduced. The maintenance of self-sustaining seizures during SE is also in part due to seizure-induced trafficking of NMDA receptors from cytosol to the synaptic membrane, which increases the number of NMDA receptors per synapse during SE (Naylor, et al., 2003, Society for Neuroscience abstract viewer and itinerary planner: 345.4; Wasterlain, et al., 2002, Ann. Neurol 52:S16; Wasterlain, et al., 2009, Epilepsia. 50:16-18; Chen, et al., 2006, Lancet Neurol. 5:246-56; Wasterlain, et al., 2006, from Status Epilepticus: Mechanisms and management. MIT Press, Boston; Naylor et al., 2013, epublication PMID: 23313318) This maladaptive change increases glutamatergic excitation at a time when there is already too much excitation in the brain, resulting in the observed seizures.

Thus, there is a need in the art for compositions and formulations for treating nerve agent-induced seizures as well as "civilian" SE. The present invention satisfies this need.

SUMMARY OF THE INVENTION

The present invention relates to a composition that has at least one GABAA receptor agonist and at least one NMDA antagonist for the treatment, amelioration, or prevention of nerve agent poisoning. In one embodiment, the at least one GABAA receptor agonist is diazepam and the at least one NMDA antagonist is ketamine. In another embodiment, the at least one GABAA receptor agonist is midazolam and the at least one NMDA antagonist is ketamine. In another embodiment, the composition also includes at least one anticonvulsant. In another embodiment, the at least one anticonvulsant is valproate. In another embodiment, the at least one anticonvulsant is brivaracetam. In another embodiment, the composition also includes at least one additional therapeutic agent.

The present invention also relates to a composition that has at least one GABAA receptor agonist and at least one NMDA antagonist for the treatment, amelioration, or prevention of a seizure induced by a disease or disorder. In one embodiment, the disease or disorder is selected from the group consisting of an acute seizure, status epilepticus (SE), epilepsy, stroke, traumatic brain injury, and cardiac arrest. In another embodiment, the at least one GABAA receptor agonist is diazepam and the at least one NMDA antagonist is ketamine. In another embodiment, the at least one GABAA receptor agonist is midazolam and the at least one NMDA antagonist is ketamine. In another embodiment, the composition also includes at least one anticonvulsant. In another embodiment, the at least one anticonvulsant is valproate. In another embodiment, the at least one anticonvulsant is brivaracetam. In another embodiment, the composition also includes at least one additional therapeutic agent.

The present invention also relates to a method of preventing, treating or ameliorating nerve agent poisoning in a subject in need thereof. The method includes the step of administering to the subject an effective amount of a composition comprising a GABAA receptor agonist and a NMDA antagonist. In one embodiment, the at least one GABAA receptor agonist is diazepam and the at least one NMDA antagonist is ketamine. In another embodiment, the at least one GABAA receptor agonist is midazolam and the at least one NMDA antagonist is ketamine. In another embodiment, the composition also includes at least one anticonvulsant. In another embodiment, the at least one anticonvulsant is valproate. In another embodiment, the at least one anticonvulsant is brivaracetam. In another embodiment, the composition also includes at least one additional therapeutic agent.

The present invention also relates to a method of preventing, treating or ameliorating a seizure induced by a disease or disorder in a subject in need thereof. The method includes the step of administering to the subject an effective amount of a composition comprising a GABAA receptor agonist and a NMDA antagonist. In one embodiment, the disease or disorder is selected from the group consisting of an acute seizure, status epilepticus (SE), epilepsy, stroke, traumatic brain injury, and cardiac arrest. In another embodiment, the at least one GABAA receptor agonist is diazepam and the at least one NMDA antagonist is ketamine. In another embodiment, the at least one GABAA receptor agonist is midazolam and the at least one NMDA antagonist is ketamine. In another embodiment, the composition also includes at least one anticonvulsant. In another embodiment, the at least one anticonvulsant is valproate. In another embodiment, the at least one anticonvulsant is brivaracetam. In another embodiment, the composition also includes at least one additional therapeutic agent.

The present invention also relates to a kit that has a composition having a therapeutically effective amount of at least one GABAA receptor agonist and at least one NMDA antagonist. In one embodiment, the composition also includes at least one anticonvulsant. In another embodiment, the composition also includes at least one additional therapeutic agent. In another embodiment, the kit also includes a device for administrating the composition. In another embodiment, the device is an autoinjector.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 5A is a graph comparing the effect of treatment on EEG power. FIG. 5B is a graph comparing the effect of treatment on time spent in an EEG burst suppression pattern (BSP). Experiments were performed using a standard rat model of SE in Wistar rats. Treatment consisted of monotherapy with diazepam (5 mg/kg), ketamine (30 mg/kg), or valproate (90 mg/kg) was compared to diazepam (1 mg/kg) combined with low-dose ketamine (10 mg/kg) and valproate (30 mg/kg). Triple therapy was more effective than higher-dose monotherapy in reducing EEG power (p<0.001), a measure of seizure severity, from a comparable baseline, and in preventing the development of a burst suppression pattern.

DETAILED DESCRIPTION

Figure 1:
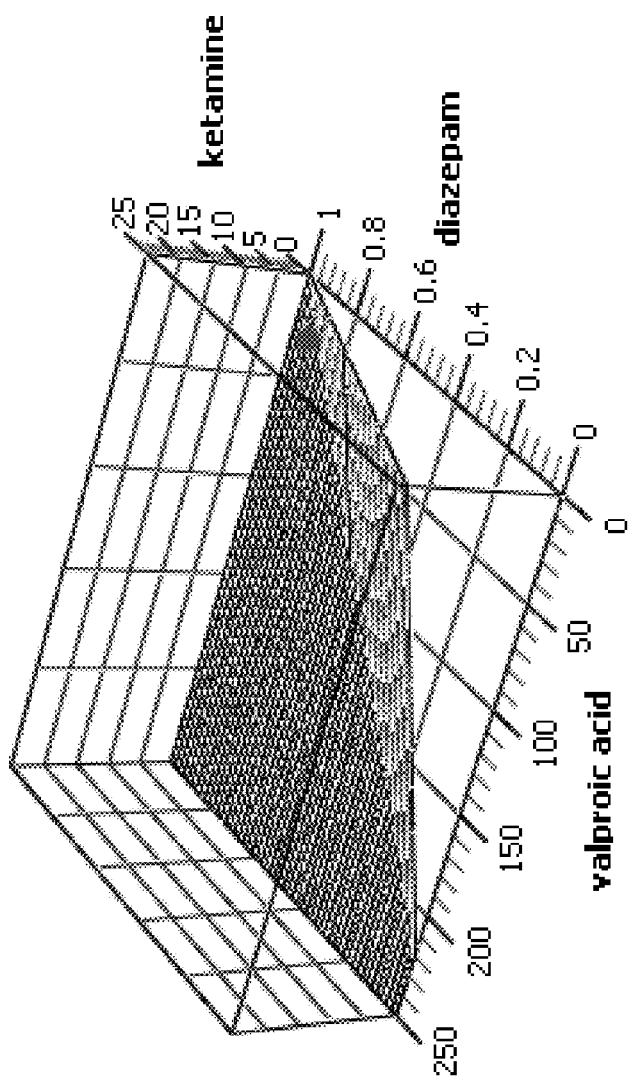
FIG. 1 is a toxicity isobologram. The red dot (score for the triple combination diazepam, ketamine, and valproate) is in the plane connecting the TD50s for individual drugs, demonstrating that the effect is simply additive.

The present invention relates to the discovery that the combination of a GABAA receptor agonist with a NMDA antagonist treats and/or prevents the onset of a seizure induced by nerve agent poisoning. Seizures are one of the main symptoms of nerve agent poisoning. Thus, the present invention provides a novel and effective approach for treating, ameliorating or preventing nerve agent poisoning using a combination of a GABAA receptor agonist with a NMDA antagonist. In certain embodiments, the GABAA receptor agonist and NMDA antagonist are used in combination with at least one anticonvulsant. In other embodiments, the GABAA receptor agonist and NMDA antagonist therapeutic are used in combination with at least one additional therapeutic agent. In another embodiment, the therapeutic agent is a muscarinic antagonist. In another embodiment, the therapeutic agent is an agent that binds to and regenerates organophosphate-inactivated acetylcholinesterases. Seizures may also be symptoms of a number of diseases and disorders. Therefore, the present invention also provides a novel and effective approach for treating, ameliorating or preventing seizures induced by a disease or disorder in a subject using a combination of a GABAA receptor agonist with an NMDA antagonist.

It is to be understood that the figures and descriptions of the present invention have been simplified to illustrate elements that are relevant for a clear understanding of the present invention, while eliminating, for the purpose of clarity, many other elements found in typical nerve agent or SE treatments. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

A "disease" is a state of health of an animal wherein the animal cannot maintain homeostasis, and wherein if the disease is not ameliorated then the animal's health is compromised.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a symptom of the disease or disorder, the frequency with which such a symptom is experienced by a subject, or both, is reduced.

The terms "subject," "patient," "individual," and the like are used interchangeably herein, and refer to any human, animal, or cells thereof whether in vitro or in situ, amenable to the methods described herein. In a non-limiting embodiment, the subject, subject or individual is a human.

A "therapeutic" treatment is a treatment administered to a subject who exhibits signs of pathology, for the purpose of diminishing or eliminating those signs.

As used herein, the term "treatment" or "treating" is defined as the application or administration of a therapeutic agent, i.e., a compound of the invention (alone or in combination with another pharmaceutical agent), to a subject, or application or administration of a therapeutic agent to an isolated tissue or cell line from a subject (e.g., for diagnosis or ex vivo applications), who has a condition contemplated herein, a symptom of a condition contemplated herein or the potential to develop a condition contemplated herein, with the purpose to cure, heal, alleviate, relieve, alter, remedy, ameliorate, improve or affect a condition contemplated herein, the symptoms of a condition contemplated herein or the potential to develop a condition contemplated herein. Such treatments may be specifically tailored or modified, based on knowledge obtained from the field of pharmacogenomics.

As used herein, the term "composition" or "pharmaceutical composition" refers to a mixture of at least one compound useful within the invention with a pharmaceutically acceptable carrier. The pharmaceutical composition facilitates administration of the compound to a subject or subject. Multiple techniques of administering a compound exist in the art including, but not limited to, intravenous, oral, aerosol, parenteral, ophthalmic, pulmonary and topical administration.

The phrase "therapeutically effective amount," as used herein, refers to an amount that is sufficient or effective to prevent or treat (delay or prevent the onset of, prevent the progression of, inhibit, decrease or reverse) a disease or condition associated with a seizure induced by nerve agent poisoning and/or a seizure induced by a disease or disorder, including alleviating symptoms of such diseases.

As used herein, the terms "effective amount," "pharmaceutically effective amount" and "therapeutically effective amount" refer to a sufficient amount of an agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

An "effective amount" of a delivery vehicle is that amount sufficient to effectively bind or deliver a compound.

As used herein, the term "potency" refers to the dose needed to produce half the maximal response ($ED_{50}$).

As used herein, the term "efficacy" refers to the maximal effect ($E_{max}$) achieved within an assay.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the language "pharmaceutically acceptable salt" refers to a salt of the administered compounds prepared from pharmaceutically acceptable non-toxic acids, including inorganic acids, organic acids, solvates, hydrates, or clathrates thereof. Examples of such inorganic acids are hydrochloric, hydrobromic, hydroiodic, nitric, sulfuric, phosphoric, acetic, hexafluorophosphoric, citric, gluconic, benzoic, propionic, butyric, sulfosalicylic, maleic, lauric, malic, fumaric, succinic, tartaric, amsonic, pamoic, p-toluenenesulfonic, and mesylic. Appropriate organic acids may be selected, for example, from aliphatic, aromatic, carboxylic and sulfonic classes of organic acids, examples of which are formic, acetic, propionic, succinic, camphorsulfonic, citric, fumaric, gluconic, isethionic, lactic, malic, mucic, tartaric, para-toluenesulfonic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic (besylate), stearic, sulfanilic, alginic, galacturonic, and the like. Furthermore, pharmaceutically acceptable salts include, by way of non-limiting example, alkaline earth metal salts (e.g., calcium or magnesium), alkali metal salts (e.g., sodium-dependent or potassium), and ammonium salts.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the subject such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the subject. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the subject. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, 6 and any whole and partial increments therebetween. This applies regardless of the breadth of the range.

Description

The present invention relates to the discovery that the combination of a GABAA receptor agonist with an NMDA antagonist treats and/or prevents the onset of a seizure induced by nerve agent poisoning. Seizures are one of the main symptoms of nerve agent poisoning. Thus, the present invention provides compositions and methods for a novel and effective approach for treating, ameliorating or preventing a nerve agent poisoning in a subject using a combination of a GABAA receptor agonist with a NMDA antagonist. In certain embodiments, the GABAA receptor agonist and NMDA antagonist are used in combination with an anticonvulsant. In certain embodiments, the GABAA receptor agonist and NMDA antagonist are used in combination with at least one anticonvulsant. In certain embodiments, the GABAA receptor agonist and NMDA antagonist are used in combination with at least one additional therapeutic agent. In another embodiment, the therapeutic agent is a muscarinic antagonist. In another embodiment, the therapeutic agent is an agent that binds to and regenerates organophosphate-inactivated acetylcholinesterases. Seizures may also be symptoms of a number of other diseases and disorders. Therefore, the present invention also provides a novel and effective approach for treating, ameliorating or preventing seizures induced by a disease or disorder in a subject using a combination of a GABAA receptor agonist with a NMDA antagonist.

The compositions and methods of the present invention are related to treating, ameliorating or preventing nerve agent poisoning through the administration of a GABAA receptor agonist and a NMDA antagonist. Examples of nerve agents include, but are not limited to, G agents such as tabun (GA), sarin (GB), soman (GD), cyclosarin (GF), and GV; V agents such as VE, VG, VM, VX, and Novichok agents. If not prevented or properly treated, nerve-agent induced seizures can quickly turn into self-sustaining seizures and uncontrolled status epilepticus (SE), potentially causing severe brain damage and/or chronic epilepsy. Treatments for seizures induced by a nerve agent that are currently in use, such as benzodiazepine, seek to reverse the reduction of functional synaptic GABAA receptors by enhancing GABAA receptor function and are administered as a monotherapy. However, these monotherapeutic treatments, which only target the GABAA receptor, can be effective as long as they are administered before the onset of seizures. Once these self-sustaining seizures have begun, they are resistant to treatment due in part to the seizure-associated internalization of synaptic GABAA receptors in key brain regions. Moreover, seizure-induced trafficking of NMDA receptors from cytosol to the synaptic membrane also leads to an increase in the number of NMDA receptors per synapse and an increase in glutamatergic excitation at a time when the brain is already overexcited. Because these currently available treatments are selective for the GABAA receptor and do not act upon the NMDA receptor, they do nothing to decrease this NMDA-based glutamatergic excitation. As such, the present invention relates to the discovery that the a therapeutic administration using a GABAA receptor agonist in combination with an agent that targets a non-GABAA site, such as a NMDA antagonist, provides an improvement over known monotherapeutic treatments for a nerve agent poisoning. The GABAA receptor agonist enhances GABAA receptor function in order to correct the loss of inhibition resulting from the reduction of functional synaptic GABAA receptors, while the NMDA antagonist reduce glutamatergic excitation by blocking NMDA receptors. In some embodiments, the GABAA receptor agonist and the NMDA antagonist are administered in combination with an anticonvulsant. The anticonvulsant enhances inhibition at a non-benzodiazepine site.

The compositions and methods of the present invention may also be useful for treating, ameliorating or preventing a seizure induced by a disease or disorder. The disease or disorder may or may not be related to nerve agent poisoning. In some embodiments, the seizures that occur in subjects with status epilepticus (SE) are often not caused by mechanisms similar to those that cause a seizure induced by nerve agent poisoning. Therefore, the compositions and methods of the present invention may also be effective in also treating a seizure induced by a disease or disorder.

Compositions

The present invention provides compositions comprised of a GABAA receptor agonist and a NMDA antagonist. Any composition comprising a GABAA receptor agonist and a NMDA antagonist is contemplated by the invention. In some embodiments, a composition of the present invention further comprises an anticonvulsant. A composition of the present invention may optionally comprise at least one additional therapeutic agent. In one embodiment, the therapeutic agent is a muscarinic antagonist. In another embodiment, the therapeutic agent is an agent that binds to and regenerates organophosphate-inactivated acetylcholinesterases.

GABAA Receptor Agonists

Any GABAA receptor agonist is contemplated for use in the compositions and methods of the present invention. Non-limiting examples of a GABAA receptor agonist include a benzodiazepine, a barbiturate, γ-aminobutyric acid (GABA), carisoprodol, chloral hydrate, etaqualone, etomidate, glutehimide, methaqualone, muscimol, a neuroactive steroid, zaleplon, zolpidem, zpoiclone, eszopiclone, and propofol. In one embodiment, the GABAA receptor agonist is a benzodiazepine. Non-limiting examples of a benzodiazepine include chlordiazepoxide, clorazepate, diazepam, flurazepam, halazepam, prazepam, lorazepam, lormetazepam, oxazepam, temazepam, clonazepam, flunitrazepam, nimetazepam, nitrazepam, adinazolam, alprazolam, estazolam, triazolam, climazolam, loprazolam, and midazolam. In certain embodiments, the GABAA receptor agonist is diazepam. In another embodiment, the GABAA receptor agonist is midazolam. In one embodiment, the GABAA receptor agonist is a barbiturate. Non-limiting examples of a bartituate include allobarbital, amobarbital, aprobarbital, alphenal, barbital, brallobarbital, pentobarbital, and phenobarbital.

NMDA Antagonists

Any NMDA antagonist is contemplated for use in the compositions and methods of the present invention. Non-limiting examples of a NMDA antagonist include dizocilpine, ifenprodil, MK801, R025-6981, TCN-201, ketamine, fluorofelbamate, felbamate, memantine, dextromethorphan, eliprodil, selfotel, Conantokin-G, -R, aptigamel (CNS1102), dynorphin A (1-13), DQP 1105, and NVP-AAM077. In a certain embodiment, the NMDA antagonist is ketamine. In one embodiment, the NMDA antagonist is non-specific. In another embodiment, the NMDA antagonist is a subunit-preferring anticonvulsant. In one embodiment, the NMDA agent is selected from the group consisting of memantine, dextromethorphan, felbamate or fluorofelbamate, or ifenprodil.

Anticonvulsants

As contemplated herein, the compositions of the present invention may further comprise an anticonvulsant. The anticonvulsant can be used to increase inhibition at non-benzodiazepine sites. Any anticonvulsant is contemplated for use in the compositions and methods of the present invention. Non-limiting examples of anticonvulsants include carbamazepine, paraldehyde, ezogabine, levetiracetam, brivaracetam, flupirtine, gabapentin, pregabalin, perampanel, felbamate, fluorofelbamate, neurosteroids, flumazenil and related compounds, fosphenyloin, lamotrigine, oxcarbazepine, phenyloin, retigabine, topiramate, and valproate. In a certain embodiment, the anticonvulsant is valproate. In another embodiment, the anticonvulsant is brivaracetam. In one embodiment, the anticonvulsant inactivates sodium channels. In another embodiment, the anticonvulsant targets potassium channels. In another embodiment, the anticonvulsant targets presynaptic vesicles.

Additional Therapeutic Agents

The compositions of the present invention may optionally include an additional therapeutic agent such that the inclusion of the therapeutic agent enhances the efficacy of the composition for preventing or treating nerve therapeutic agent poisoning. The compositions of the present invention may also optionally include an additional therapeutic agent such that the inclusion of the therapeutic agent enhances the efficacy of the composition for preventing or treating nerve agent poisoning. The therapeutic agent may be any therapeutic agent known in the art to treat nerve agent poisoning, as understood by one skilled in the art. In some embodiments, the therapeutic agent is a muscarinic antagonist. Examples of muscarinic antagonists include, but are not limited to, atropine, scopolamine, hydroxyzine, ipratropium, tropicamide, pirenzepine, diphenhydramine, dimenhydrinate, dicyclomine, flavoxate, lxybutynin, tiotropium, cyclopentolate, atropine methonitrate, trihexyphenidyl (benzhexyl), tolterodine, solifenacin, darifenacin, benzatropine, mebeverine, and procyclidine. In one embodiment, the therapeutic agent is atropine. In another embodiment, the therapeutic agent is scopolamine. In other embodiments, the therapeutic agent is an agent that binds to organophosphate-inactivated acetylcholinesterases. These therapeutic agents regenerate a cholinesterase bound to a cholinesterase inhibitor by attaching to the cholinesterase inhibitor and removing it from the cholinesterase, thus allowing the cholinesterase to regain its normal function. Examples of a therapeutic agent that binds to organophosphate-inactivated acetylcholinesterases include, but are not limited to, oximes such as pralidoxime, obidoxime, methoxime, HI-6, Hlo-7, and TMB-4. In one embodiment, the therapeutic agent is pralidoxime.

Methods of the Invention

The invention includes a method of treating, ameliorating or preventing nerve agent poisoning in a subject in need thereof. The method comprises administering to the subject an effective amount of a therapeutic composition comprising a GABAA receptor agonist and a NMDA antagonist.

The invention includes a method of treating, ameliorating or preventing nerve agent poisoning in a subject in need thereof. The method comprises administering to the subject an effective amount of a therapeutic composition comprising a GABAA receptor agonist and a NMDA antagonist, and further administering to the subject an anticonvulsant.

The invention includes a method of treating, ameliorating or preventing nerve agent poisoning in a subject in need thereof. The method comprises administering to the subject an effective amount of a therapeutic composition comprising a GABAA receptor agonist and a NMDA antagonist, and further administering to the subject an additional therapeutic agent. In one embodiment, the therapeutic agent is a muscarinic antagonist. In another embodiment, the therapeutic agent is an agent that binds to and regenerates organophosphate-inactivated acetylcholinesterases.

In one embodiment, administering the NMDA antagonist allows for administering a lower dose of the GABAA receptor agonist, as compared to the dose of the GABAA receptor agonist alone that is required to achieve similar results in treating, ameliorating or preventing nerve agent poisoning in the subject. In another embodiment, the GABAA receptor agonist and the NMDA antagonist are co-administered to the subject. In yet another embodiment, the GABAA receptor agonist and the NMDA antagonist are co-formulated and co-administered to the subject.

In one embodiment, administering the anticonvulsant agent to the subject allows for administering a lower dose of the GABAA receptor agonist and/or the NMDA antagonist, as compared to the dose of the GABAA receptor agonist and/or the NMDA antagonist alone that is required to achieve similar results in treating, ameliorating or preventing nerve agent poisoning in the subject. In another embodiment, the GABAA receptor agonist, the NMDA antagonist and the anticonvulsant are co-administered to the subject. In yet another embodiment, the GABAA receptor agonist, the NMDA antagonist and the anticonvulsant are co-formulated and co-administered to the subject.

In one embodiment, administering the additional therapeutic agent to the subject allows for administering a lower dose of the GABAA receptor agonist and/or the NMDA antagonist, as compared to the dose of the GABAA receptor agonist and/or the NMDA antagonist alone that is required to achieve similar results in treating, ameliorating or preventing nerve agent poisoning in the subject. In another embodiment, the GABAA receptor agonist, the NMDA antagonist, and the therapeutic agent are co-administered to the subject. In yet another embodiment, the GABAA receptor agonist, the NMDA antagonist, and the therapeutic agent are co-formulated and co-administered to the subject.

In one embodiment, the subject is a mammal. In another embodiment, the mammal is a human.

Seizures Induced by a Disease or Disorder

As contemplated herein, the compositions and methods of the present invention may also be useful for treating, ameliorating or preventing a seizure induced by a disease or disorder. A seizure induced by any disease or disorder may be treated by the compositions and methods of the present invention such that the seizure is caused by mechanisms similar to a seizure induced nerve agent poisoning. Non-limiting examples of a disease or disorder that may be treated using the compounds and methods of the present invention include acute seizures, status epilepticus (SE), epilepsy, stroke, traumatic brain injury, cardiac arrest, drug use, drug withdrawal, alcohol withdrawal, a bacterial, fungal, or viral infection, a tumor, a metabolic encephalopathy associated with hypo- or hyperglycemia, hypo- or hypernatremia, acidosis, alkalosis, hepatic, uremic hypoxic-ischemic or other encephalopathy, an autoimmune or inflammatory process, adegenerative brain disease, and a gene defect.

Combination and Concurrent Therapies

The compositions of the present invention are intended to be useful in combination with one or more additional compounds. The compositions of the present invention are also intended to be useful when used concurrently with one or more additional compounds. These additional compounds may comprise compounds of the present invention or therapeutic agents known to treat, prevent, or reduce the symptoms or effects of nerve agent poisoning. Such compounds include, but are not limited to, anticonvulsants, AEDs, drugs which alter synaptic transmission, muscarinic antagonists, and agents that bind to organophosphate-inactivated acetylcholinesterases.

In non-limiting examples, the compositions of the invention may be used in combination with one or more therapeutic agents (or a salt, solvate or prodrug thereof) selected from the group consisting of anticonvulsants, including but are not limited to carbamazepine, paraldehyde, ezogabine, levetiracetam, brivaracetam, flupirtine, gabapentin, lamotrigine, oxcarbazepine, phenyloin, retigabine, topiramate, and valproate;

muscarinic antagonists, including but are not atropine, scopolamine, hydroxyzine, ipratropium, tropicamide, pirenzepine, diphenhydramine, dimenhydrinate, dicyclomine, flavoxate, lxybutynin, tiotropium, cyclopentolate, atropine methonitrate, trihexyphenidyl (benzhexyl), tolterodine, solifenacin, darifenacin, benzatropine, mebeverine, and procyclidine;

agents that bind to organophosphate-inactivated acetylcholinesterases, including but are not limited to oximes, such as pralidoxime, obidoxime, methoxime, HI-6, Hlo-7, and TMB-4.

In one embodiment, a composition of the present invention comprises diazepam and ketamine. In another invention, the composition comprises midazolam and ketamine.

In another embodiment, the composition comprises diazepam, ketamine, and valproate. In another embodiment, the composition comprises diazepam, ketamine, and brivaracetam. In another embodiment, the composition comprises midazolam, ketamine, and valproate. In another embodiment, the composition comprises midazolam, ketamine, and brivaracetam.

A synergistic effect may be calculated, for example, using suitable methods such as, for example, the Sigmoid-$E_{max}$ equation (Holford & Scheiner, 1981, Clin. Pharmacokinet 6429-453), the equation of Loewe additivity (Loewe & Muischnek, 1926, Arch. Exp. Pathol Pharmacol. 114:313-326) and the median-effect equation (Chou & Talalay, 1984, Adv. Enzyme Regul. 22:27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Administration/Dosage/Formulations

The regimen of administration may affect what constitutes an effective amount. The therapeutic formulations may be administered to the subject either prior to or after the onset of nerve agent poisoning. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a subject, preferably a mammal, more preferably a human, may be carried out using known procedures, at dosages and for periods of time effective to treat nerve agent poisoning in the subject. An effective amount of the composition necessary to achieve a therapeutic effect may vary according to factors such as the state of the disease or disorder in the subject; the age, sex, and weight of the subject; and the ability of the therapeutic compound to treat GABAA and/or glutamate-receptors related disorders or diseases in the subject. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a composition of the invention is from about 0.1 and 5,000 mg/kg of body weight/per day. One of ordinary skill in the art would be able to study the relevant factors and make the determination regarding the effective amount of the composition without undue experimentation.

Actual dosage levels of the active ingredients in the pharmaceutical compositions of this invention may be varied so as to obtain an amount of the active ingredient that is effective to achieve the desired therapeutic response for a particular subject, composition, and mode of administration, without being toxic to the subject.

In particular, the selected dosage level depends upon a variety of factors including the activity of the particular composition employed, its toxicity, the time of administration, the rate of excretion of the compound, the duration of the treatment, other drugs, compounds or materials used in combination with the compound, the age, sex, weight, condition, general health and prior medical history of the subject being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compositions of the invention employed in the pharmaceutical composition at levels lower than that required in order to achieve the desired therapeutic effect and gradually increase the dosage until the desired effect is achieved.

In particular embodiments, it is especially advantageous to formulate the composition in dosage unit form for ease of administration and uniformity of dosage. Dosage unit form as used herein refers to physically discrete units suited as unitary dosages for the subjects to be treated; each unit containing a predetermined quantity of therapeutic composition calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic composition for the treatment of nerve agent poisoning.

In one embodiment, the compositions of the invention are formulated using one or more pharmaceutically acceptable excipients or carriers. In one embodiment, the pharmaceutical compositions of the invention comprise a therapeutically effective amount of a composition of the invention and a pharmaceutically acceptable carrier. In some embodiments, the GABAA receptor agonist and the NMDA antagonist and/or the anticonvulsant are each dissolved in a solvent and injected into the subject simultaneously using an autoinjector comprised of a plurality of needles. In one embodiment, the GABAA receptor agonist and the NMDA antagonist and/or the anticonvulsant are each dissolved in the same solvent. In one embodiment, the GABAA receptor agonist and the NMDA antagonist and/or the anticonvulsant are each dissolved in a different solvent. In one embodiment, the autoinjector comprises two needles. In another embodiment, the autoinjector comprises three needles.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it is preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin. In one embodiment, the pharmaceutically acceptable carrier is not DMSO alone.

In one embodiment, the compositions of the invention are administered to the subject in dosages that range from one to five times per day or more. In another embodiment, the compositions of the invention are administered to the subject in range of dosages that include, but are not limited to, once every day, every two, days, every three days to once a week, and once every two weeks. It is readily apparent to one skilled in the art that the frequency of administration of the various combination compositions of the invention varies from individual to individual depending on many factors including, but not limited to, age, disease or disorder to be treated, gender, overall health, and other factors. Thus, the invention should not be construed to be limited to any particular dosage regime and the precise dosage and composition to be administered to any subject is determined by the attending physical taking all other factors about the subject into account.

Compositions of the invention for administration may be in the range of from about 1 µg to about 10,000 mg, about 20 µg to about 9,500 mg, about 40 µg to about 9,000 mg, about 75 µg to about 8,500 mg, about 150 µg to about 7,500 mg, about 200 µg to about 7,000 mg, about 3050 µg to about 6,000 mg, about 500 µg to about 5,000 mg, about 750 µg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments therebetween.

In some embodiments, the dose of a composition of the invention is from about 1 mg and about 2,500 mg. In some embodiments, a dose of a composition of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In one embodiment, the present invention is directed to a packaged pharmaceutical composition comprising a container holding a therapeutically effective amount of a composition of the invention, alone or in combination with one or more pharmaceutical agents; and instructions for using the composition to treat, prevent, or reduce one or more symptoms of nerve agent poisoning in a subject.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

Routes of administration of any of the compositions of the invention include oral, nasal, rectal, intravaginal, parenteral, buccal, sublingual or topical. The compositions for use in the invention may be formulated for administration by any suitable route, such as for oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For oral administration, the compositions of the invention may be in the form of tablets or capsules prepared by conventional means with pharmaceutically acceptable excipients such as binding agents (e.g., polyvinylpyrrolidone, hydroxypropylcellulose or hydroxypropylmethylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e. drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) melt.

The present invention also includes a multi-layer tablet comprising a layer providing for the delayed release of one or more compounds of the invention, and a further layer providing for the immediate release of a medication for treatment of Parkinson's Disease. Using a wax/pH-sensitive polymer mix, a gastric insoluble composition may be obtained in which the active ingredient is entrapped, ensuring its delayed release.

Parenteral Administration

For parenteral administration, the compositions of the invention may be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents may be used.

Additional Administration Forms

Additional dosage forms of this invention include dosage forms as described in U.S. Pat. Nos. 6,340,475; 6,488,962; 6,451,808; 5,972,389; 5,582,837; and 5,007,790. Additional dosage forms of this invention also include dosage forms as described in U.S. Patent Applications Nos. 20030147952; 20030104062; 20030104053; 20030044466; 20030039688; and 20020051820. Additional dosage forms of this invention also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Controlled Release Formulations and Drug Delivery Systems

In one embodiment, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compositions may be formulated with a suitable polymer or hydrophobic material which provides sustained release properties to the compositions. As such, the compositions for use in the method of the invention may be administered in the form of microparticles, for example, by injection or in the form of wafers or discs by implantation.

In one embodiment of the invention, the compositions of the invention are administered to a subject, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosing

The therapeutically effective amount or dose of a composition of the present invention depends on the age, sex and weight of the subject, the current medical condition of the subject and the progression of sigma-receptor related disorders or diseases in the subject being treated. The skilled artisan is able to determine appropriate dosages depending on these and other factors.

A suitable dose of a composition of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

It is understood that the amount of composition dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

In the case wherein the subject's status does improve, upon the doctor's discretion the administration of a composition of the invention is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the subject's conditions has occurred, a maintenance dose is administered if necessary. Subsequently, the dosage or the frequency of administration, or both, is reduced, as a function of the viral load, to a level at which the improved disease is retained. In one embodiment, subjects require intermittent treatment on a long-term basis upon any recurrence of symptoms and/or infection.

The composition for use in the method of the invention may be formulated in unit dosage form. The term "unit dosage form" refers to physically discrete units suitable as unitary dosage for subjects undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Toxicity and therapeutic efficacy of such therapeutic regimens are optionally determined in cell cultures or experimental animals, including, but not limited to, the determination of the $LD_{50}$ (the dose lethal to 50% of the population), the TD50 (dose which reaches a determined level of toxicityn in 50% of subjects), and the $ED_{50}$ (the dose therapeutically effective in 50% of the population). The dose ratio between the toxic and therapeutic effects is the therapeutic index, which is expressed as the ratio between $LD_{50}$ and $ED_{50}$. Capsid assembly inhibitors exhibiting high therapeutic indices are preferred. The data obtained from cell culture assays and animal studies are optionally used in formulating a range of dosage for use in human. The dosage of such capsid assembly inhibitors lies preferably within a range of circulating concentrations that include the $ED_{50}$ with minimal toxicity. The dosage optionally varies within this range depending upon the dosage form employed and the route of administration utilized.

Those skilled in the art recognizes, are able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

Kits

Embodiments of the invention also provide articles of manufacture and kits which include agents and compositions used in the methods of the invention (e.g. a GABAA receptor agonist, an NMDA antagonist, an anticonvulsant agent, etc.). In typical embodiments of the invention, the kit comprises one or more containers, typically with a label. Typically, the label on the one or more containers indicates that the one or more agents is used as a prophylaxis for and/or in the treatment of nerve agent poisoning. Such labels may also indicate directions for use, such as those described herein. Kits may further include other devices and/or materials desirable from a commercial and user standpoint, including devices used in the administration of such agents, for example one or more autoinjectors designed to deliver a dose of an agent (e.g. one comprising a spring-loaded syringe), as well as other materials such as diluents, filters, needles, syringes, and package inserts with instructions for use.

A GABAA receptor agonist and a NMDA antagonist may be provided in the kit as a single dose or as multiple doses, alone or in combination with one or more doses of at least one anticonvulsant and/or with one or more doses of at least one additional agent. In some embodiments, a single dose is a therapeutically effective amount. Determination of a therapeutically effective amount and timing of administration of a given compound is well within the capabilities of those skilled in the art, especially in light of the detailed disclosure herein.

EXPERIMENTAL EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Example 1: Polytherapy for the Treatment of Status Epilepticus (SE)

As described herein, combining GABAA receptor agonist, such as a benzodiazepine, with an NMDA antagonist greatly improves the efficacy of treatment for SE when compared to a monotherapy, where only one of a benzodiazepine or a NMDA antagonist is added. Benzodiazepine stimulation, while useful, is unlikely to fully restore inhibition because there are not enough GABAA receptors left in the synapse for inhibition to recover. Therefore, the addition of another therapeutic agent that acts on a different site from GABAA, such as a NMDA antagonist, in combination with a GABAA receptor agonist and optionally with another enhancer of inhibition, was found to be more effective and less toxic than a monotherapy for treating cholinergic SE.

Examples of effective therapeutic compositions include: diazepam, ketamine, and valproate; diazepam, ketamine, and brivaracetam; midazolam, ketamine and valproate; and midazolam, ketamine and brivaracetam.

Also described herein are results from a surrogate model of nerve agent exposure in rodents demonstrating that certain combinations of anticonvulsant drugs [combinations of two drugs (a GABA receptor agonist and an NMDA antagonist) or three drugs (a GABA receptor agonist, a NMDA antagonist, and an additional therapeutic agent)] can have a powerful synergic effect and stop seizures even when the injection is delayed 20 to 30 minutes after the onset of the seizure or after benzodiazepine pharmacoresistance has been established. An antidote using the compositions of the present invention may be useful in reducing the number of casualties and attenuating the brain injuries resulting from an attack with a nerve agent. Compositions of the present invention may also be useful in the treatment of status epilepticus (SE), an acute, life-threatening event which is a manifestation of epilepsy or other illnesses unrelated to nerve agent exposure. Also demonstrated herein is that, in a standard animal model of status epilepticus (SE), the response to treatment with a three-drug therapy was superior to the response to treatment with a benzodiazepine monotherapy.

The materials and methods employed in these experiments are now described.

A rat model of severe SE induced by high-dose lithium and pilocarpine was used (see, e.g. Tetz, et al. 2006. Development of a rat pilocarpine model of seizure/status epilepticus that mimics chemical warfare nerve agent exposure. *Toxicology Industr. Health;* 22:255-66), and was designed to mimic the effects of 1.2×LD50 dose of nerve agent. Other experiments used a routine lithium/pilocarpine model of SE (see, e.g. Suchomelova L, et al. Treatment of experimental status epilepticus in immature rats: dissociation between anticonvulsant and antiepileptogenic effects. *Ped. Res.* 2006; 59:237-243; Lopez-Meraz M L, et al. Distinct caspase pathways mediate necrosis and apoptosis in subpopulations of hippocampal neurons after status epilepticus. *Epilepsia* 2010; 51(Suppl 3):56-60). The EEG was recorded for 24 hrs after onset, and intermittently thereafter. Because of applications of the present invention to battlefield or terrorism situations, the ability to move about and to retain consciousness was selected as key measures of drug toxicity. Outcome measures were termination of SE, using a variety of clinical and EEG criteria, and reduction of neuronal injury and reduction of the spontaneous recurrent seizures one month or more after SE. Treatment allosterically stimulated remaining synaptic GABAA receptors with benzodiazepines. A drug was added which enhanced inhibition at a non-GABA site, since GABA agonists can only partially restore GABA inhibition in this model. Excitation was reduced due to an increased number of synaptic NMDA receptors with NMDA antagonists. Treatment was administered intraperitoneally after benzodiazepine pharmacoresistance was established. The cholinergic antagonist atropine or scopolamine was administered in both the monotherapy and polytherapy group for two reasons: a) to neutralize the cholinergic component of seizures and be able to separate its effect from self-sustaining seizures; b) to mimic the field situation where soldiers or victims of terrorist or accidental exposure first receive atropine injection and later an anticonvulsant.

The results of these experiments are now described.

The effect of mono-, bi- and tri-therapy was compared in a rat model of severe SE induced by high-dose lithium and pilocarpine, which mimics chemical warfare nerve agent exposure (see, e.g. Tetz L M, et al. Development of a rat pilocarpine model of seizure/status epilepticus that mimics chemical warfare nerve agent exposure. *Toxicology Industr. Health* 2006; 22:255-66).

Monotherapy: Benzodiazepine monotherapy reduced mortality from 52% to 7% (5 mg/kg diazepam) or less (10-20 mg/kg) but did not stop seizures even at a dose of 20 mg/kg (Dz20), which induced coma (toxicity score 11.2±0.9). The number of post-treatment seizures was 100±7 in sham-injected controls and 100±8 after 20 mg/kg DZ (N.S.). Monotherapy with ketamine 10 mg/kg (K), valproate 30 mg/kg (V), brivaracetam 10 mg/kg (Brv), diazepam (1, 5 or 10, or 20 mg/kg), and other antiepileptic drugs also failed to stop SE. Diazepam (1 mg/kg, 5 mg/kg, 10 mg/kg, or 20 mg/kg) did not reduce seizure frequency or the Hjorth function compared to controls not receiving anticonvulsants (atropine group). These results demonstrate that the model is appropriate for these studies, since it is able to test SE that has become pharmacoresistant to even high doses of a benzodiazepine (Table 1).

TABLE 1

Evidence of Benzodiazepine Pharmacoresistance in the Tetz model of SE in Wistar rats

| | Treatment | Outcome | Seizures/day | Spikes/day | Hjorth 1 hr | Hjorth 6 hr |
|---|---|---|---|---|---|---|
| Mean | Atropine Only Control | 10/19 died | 76 | 2567 | 3502 | 11662 |
| SD | | | 36 | 2828 | 1496 | 7206 |
| SE | | | 12 | 942.6 | 499 | 2402 |
| Mean | Dz 5 mg/kg after 2 hr delay | 4/5 died | 83 | | 2880 | |
| SD | | | 30 | | 1160 | |
| SE | | | 22 | | 670 | |
| Mean | Dz 5 mg/kg after 1 hr delay | 3/4 died | 101 | | 3588 | |
| SD | | | 36 | | 867 | |
| SE | | | 21 | | 500 | |
| Mean | Dz 1 mg/kg | 4/7 died | 107 | 5179 | 1780 | 6534 |
| SD | | | 18 | | 146 | 2757 |
| SE | | | 10 | | 84 | 1378 |
| Mean | Dz 5 mg/kg | | 115 | 2508 | 2312 | 5398 |
| SD | | | 88 | 2277 | 1683 | 5105 |
| SE | | | 24 | 631 | 486 | 1416 |
| Mean | Dz 10 mg/kg | | 89 | 1134 | 3362 | 5398 |
| SD | | | 29 | 351 | 190 | 678 |
| SE | | | 17 | 203 | 110 | 392 |
| Mean | Dz 20 mg/kg | | 100 | 1077 | 2924 | 8238 |

TABLE 1-continued

Evidence of Benzodiazepine Pharmacoresistance in the Tetz model of SE in Wistar rats

| Treatment | Outcome | Seizures/day | Spikes/day | Hjorth 1 hr | Hjorth 6 hr |
|---|---|---|---|---|---|
| SD | | 18 | 723 | 1059 | 3261 |
| SE | | 8 | 323 | 474 | 1459 |

Seizure frequency (number of seizures in the first 24 hrs) and the Hjorth function, measured over the first 1 hr or 6 hrs after treatment, are measures of the severity of SE.

Effect of tritherapy on post-treatment seizures: Combinations of low-dose diazepam (1 mg/kg) with ketamine (10 mg/kg) and valproate (30 mg/kg) (Dz1+K+V), reduced the number of post-treatment seizures to 8±2 (p<0.001 vs. Dz or C) while preserving the righting reflex (toxicity score 1±0.4) (Table 2). A combination of diazepam (1 mg/kg) with ketamine (10 mg/kg) and brivaracetam (10 mg/kg) (Dz1+K+Brv), reduced the number of post-treatment seizures to 8±4 (p<0.01 vs. DZ or C) and preserved the righting reflex (toxicity score 1.4±0.9), while DZ20 severely impaired locomotion and the righting reflex (toxicity score 11.2±0.9) (Table 3). Some two-drug combinations were also significantly more effective than monotherapy in this model.

TABLE 2

Monotherapy, Bitherapy and Polytherapy using Diazepam, Ketamine and Valproate in the Tetz model of SE in Wistar rats

| | Treatment | Outcome | Seizures/day | Spikes/day | Hjorth 1 hr |
|---|---|---|---|---|---|
| Mean | Atropine Only | 10/19 died | 76 | 2567 | 3502 |
| SD | Control | | 36 | 2828 | 1496 |
| SE | | | 12 | 942.6 | 499 |
| Mean | Dz 1 mg/kg | 4/7 died | 107 | 5179 | 1780 |
| SD | | | 18 | | 146 |
| SE | | | 10 | | 84 |
| Mean | Ket 10 mg/kg | | 35 | 2166 | 3681 |
| SD | | | 8 | 2595 | 2194 |
| SE | | | 3 | 1059 | 895.6 |
| | Val 30 mg/kg | 3/4 died | | | |
| Mean | Ket 10 + Dz 1 | 1/12 died | 27 | 328 | 546 |
| SD | | | 58 | 739 | 587 |
| SE | | | 18 | 234 | 185 |
| Mean | Val 30 + Ket 10 | | 46 | 2649 | 2091 |
| SD | | | 34 | 2118 | 1787 |
| SE | | | 13 | 800.6 | 676 |
| Mean | Val 30 + Dz 1 | | 41 | 7750 | 1151 |
| SD | | | 66 | 7997 | 1047 |
| SE | | | 66 | 3265 | 428 |
| Mean | Val 30 + Ket 10 + | | 8 | 152.2 | 518 |
| SD | Dz 1 | | 6 | 143.9 | 414 |
| SE | | | 2 | 58.74 | 162 |

Seizure frequency (number of seizures in the first 24 hrs), the number of spikes in 24 hrs, and the Hjorth function, measured over the first 1 hr after treatment, are measures of the severity of SE

TABLE 3

Monotherapy, Bitherapy and Polytherapy using Diazepam, Ketamine and Brivaracetam in the Tetz model

| | Treatment | Outcome | Seizures/day | Spikes/day | Hjorth 1 hr |
|---|---|---|---|---|---|
| Mean | Atropine Only | 10/19 died | 76 | 2567 | 3502 |
| SD | Control | | 36 | 2826 | 1496 |
| SE | | | 12 | 942.6 | 499 |
| Mean | Dz 1 mg/kg | 4/7 died | 107 | 5179 | 1780 |
| SD | | | 18 | | 146 |
| SE | | | 10 | | 84 |
| Mean | Ket 10 mg/kg | | 35 | 2166 | 3681 |
| SD | | | 8 | 2595 | 2194 |
| SE | | | 3 | 1059 | 895.6 |
| | Briv 10 mg/kg | 5/5 died | | | |
| Mean | Ket 10 + Dz 1 | 1/12 died | 27 | 328 | 546 |
| SD | | | 58 | 739 | 587 |
| SE | | | 18 | 234 | 185 |
| Mean | Brv 10 + Ket 10 | 1/5 died | 26 | 5444 | 1428 |
| SD | | | 19 | 1613 | 739.1 |
| SE | | | 9 | 806.5 | 370 |
| Mean | Brv 10 + Dz 1 | 1/5 died | 43 | 13165 | 969 |
| SD | | | 39 | 18598 | 823 |
| SE | | | 23 | 10738 | 475 |
| Mean | Brv 10 + Ket 10 + | | 7.7 | 1111 | 592 |
| SD | Dz 1 | | 12 | 2836 | 674 |
| SE | | | 3.8 | 896.8 | 213 |

Figure 2:
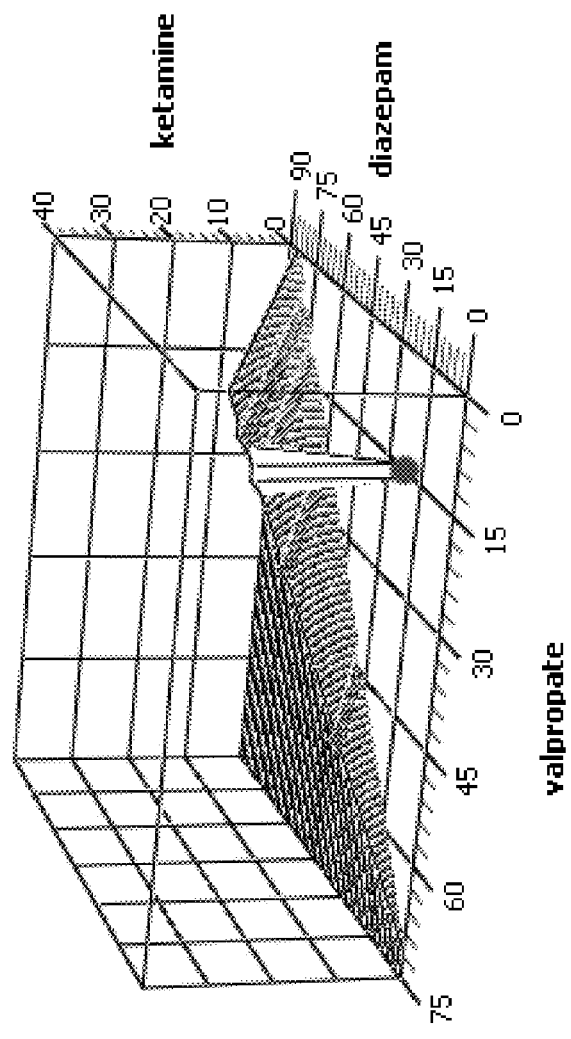
FIG. 2 is an efficacy isobologram. The red dot (combined treatment) is well below the plane connecting the TD50s for individual drugs, showing that the therapeutic effect is obtained with a much smaller dose than expected by simple addition, e.g. there is synergism between drugs.

Seizure frequency (number of seizures in 24 hrs), the number of spikes in 24 hrs, and the Hjorth function, measured over the first 1 hr after treatment, are measures of the severity of SE Effect of tritherapy on EEG power (a measure of SE severity): Compared to high-dose diazepam monotherapy (20 mg/kg), very low dose diazepam (1 mg/kg) combined with ketamine 10 mg/kg and valproate 30 mg/kg or brivaracetam 10 mg/kg (all low dose) reduced the time needed for the EEG power to return to 2× pre-seizure baseline (p<0.01) and reduced seizure number while causing little toxicity (toxicity score after Dz20=11±1.5, after Dz1+Ket10+Val30=0.6±0.3, after Dz1+Ket10+Brv10=0.5±0.2). Isobolograms for both triple combinations showed a simply additive (non-synergistic) effect for toxicity (FIG. 1), but suggested a highly synergistic effect for the time needed to reduce EEG power to 2× pre-seizure baseline and for other measure of therapeutic efficacy (FIG. 2). In other studies, EEG power after treatment using midazolam, ketamine, and valproate as a tritherapy showed a benefit of (valproate 90 mg/kg+ketamine 30 mg/kg+midazolam 3 mg/kg) over higher dose monotherapy (Table 4).

TABLE 4

Monotherapy and Polytherapy using Midazolam, Ketamine and Valproate

| | Treatment | EEG power at time of treatment (decibels) | Power integrals 1 hr after treatment in decibel minutes |
|---|---|---|---|
| Mean | Control | 19 | 1000.2 |
| SD | | 2 | 150.7 |
| Mean | Val 270 mg/kg | 19.8 | 940.5 |
| SD | | 3.2 | 124.9 |

TABLE 4-continued

Monotherapy and Polytherapy using
Midazolam, Ketamine and Valproate

| | Treatment | EEG power at time of treatment (decibels) | Power integrals 1 hr after treatment in decibel minutes |
|---|---|---|---|
| Mean | Ket 90 mg/kg | 23.7 | 436.7 |
| SD | | 1.7 | 419.3 |
| Mean | Mdz 9 mg/kg | 23.4 | 716.7 |
| SD | | 3.2 | 253 |
| Mean | Val 90 + Ket 30 + Mdz 3 | 19.3 | −163.5 |
| SD | | 2.1 | 79.5 |

This model was performed in Sprague-Dawley rats, using scopolamine (10 mg/kg) instead of atropine in all groups, and treatment was given 40 min. after induction of SE. EEG power at the time of treatment was similar in all groups.

Figure 3:
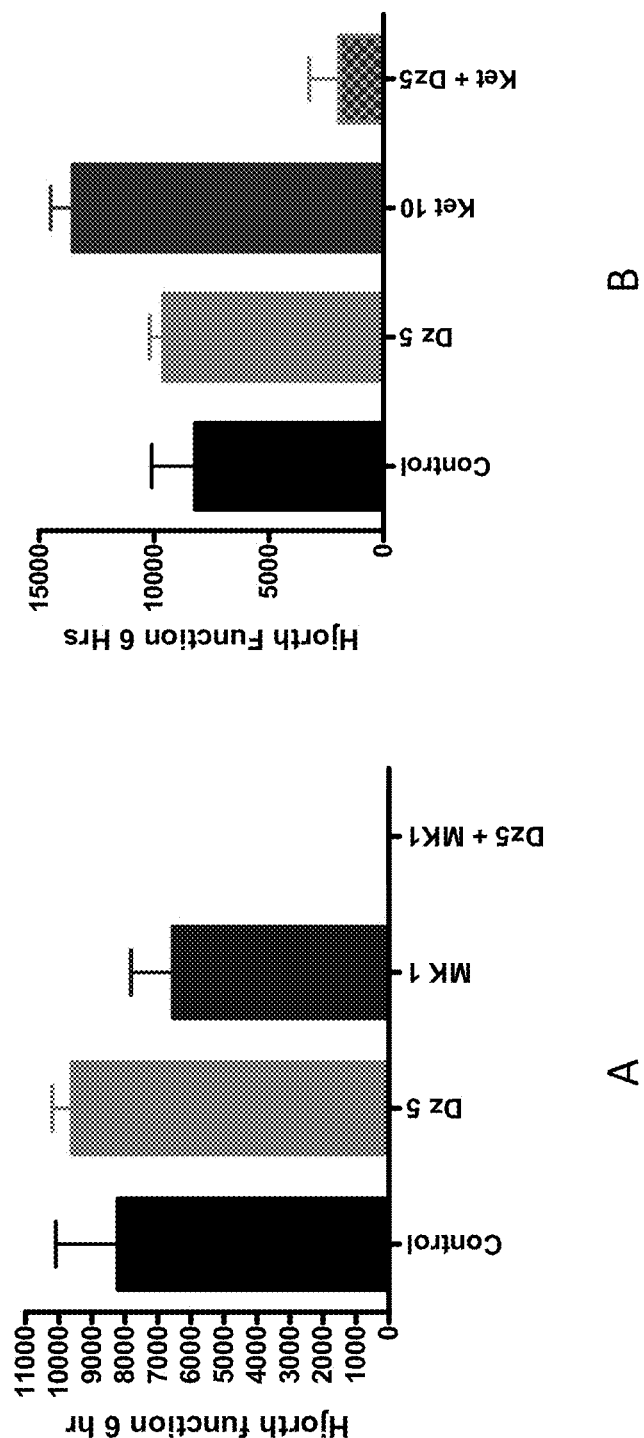
FIG. 3 is a chart depicting the effect of dual treatment with a GABAA receptor agonist and an NMDA antagonist in the Tetz model of SE. In the Tetz model of SE, Hjorth function, a measure of seizure severity which emphasizes EEG power, was measured over the first 6 hrs after treatment. Diazepam 5 mg/kg, Ketamine 10 mg/kg, or dizocilpine (MK-801. 1 mg/kg) did not reduce Hjorth function compared to controls not receiving anticonvulsants. However, when a GABAA receptor agonist (diazepam) was combined with an NMDA antagonist (ketamine or dizocilpine), Hjorth function was reduced, suggesting that these combinations of a GABAA receptor agonist with an NMDA antagonist are more effective than either monotherapy.

Effect of bitherapy on EEG power: Monotherapy with a moderate dose of Diazepam (5 mg/kg), Ketamine (10 mg/kg), or dizocilpine (MK-801-1 mg/kg) did not reduce seizure severity compared to controls not receiving anticonvulsants. However, bitherapy that combines a GABAA receptor agonist (diazepam) with an NMDA antagonist (ketamine or dizocilpine) was effective to reduce the seizure severity (FIG. 3).

Figure 4:
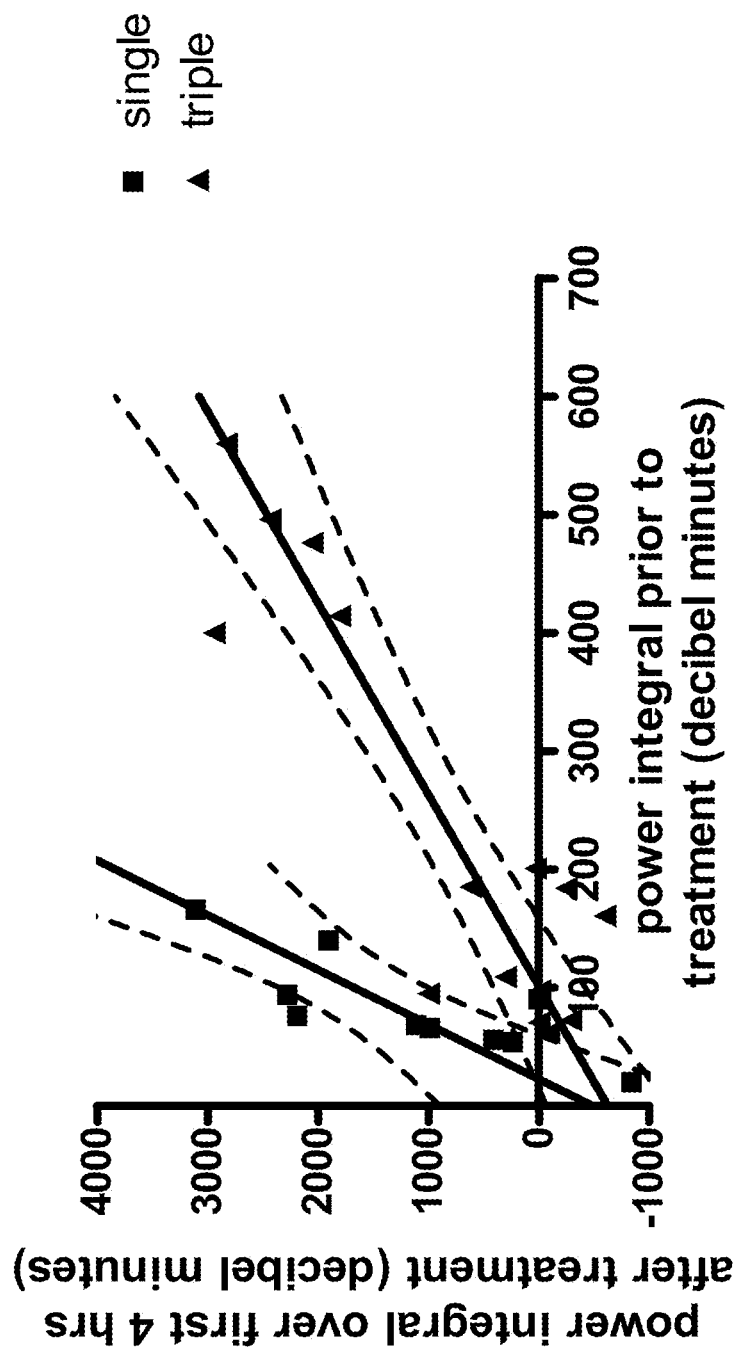
FIG. 4 is a graph comparing the effect on EEG power of 5 mg/kg diazepam to those of 1 mg/kg diazepam combined with low-dose ketamine (10 mg/kg) and valproate (30 mg/kg) using a standard rat model of SE (see, e.g. Lopez-Meraz et al. Distinct caspase pathways mediate necrosis and apoptosis in subpopulations of hippocampal neurons after status epilepticus. *Epilepsia* 2010; 51(Suppl 3):56-60). Triple therapy was more effective than higher-dose monotherapy in reducing EEG power (p<0.001), a measure of seizure severity, from a comparable baseline.

It was also found that tritherapy was more effective than monotherapy in a standard model of SE, induced by moderate dose of lithium and pilocarpine (FIG. 4).

Figure 5:
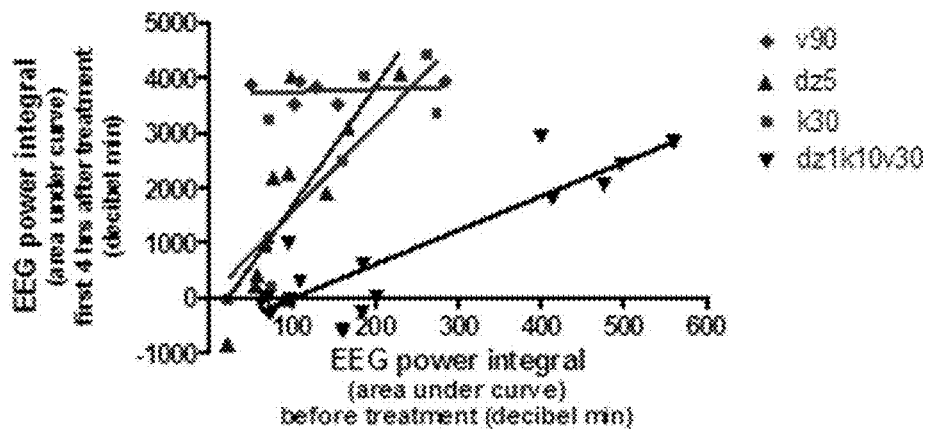
FIG. 5, comprised of FIGS. 5A-5B, compares monotherapy treatments to triple therapy treatments.
Figure 5:
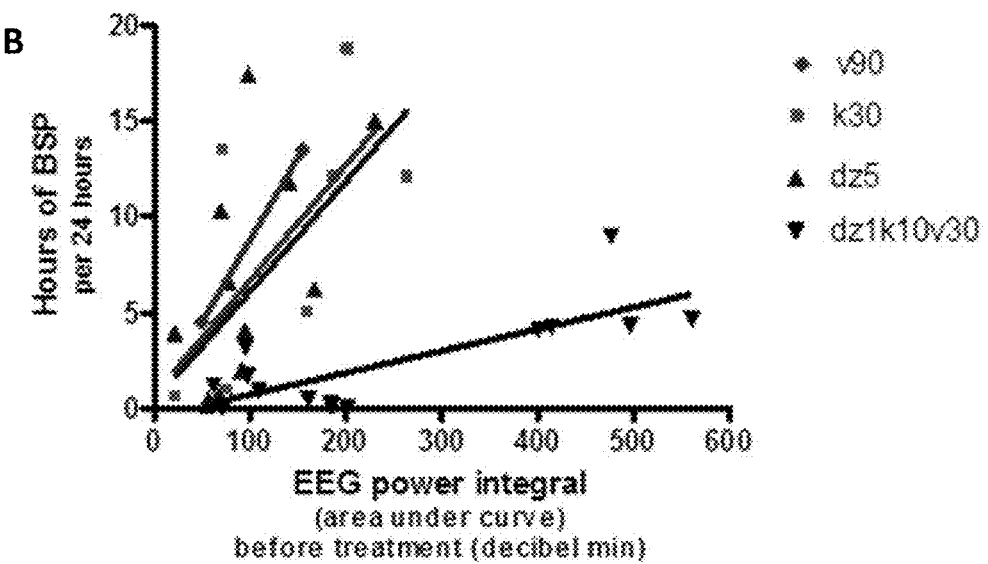

Triple therapy was more effective than higher-dose monotherapy in reducing EEG power (p<0.001), a measure of seizure severity, from a comparable baseline, and in preventing the development of a burst suppression pattern (FIG. 5).

Figure 6:
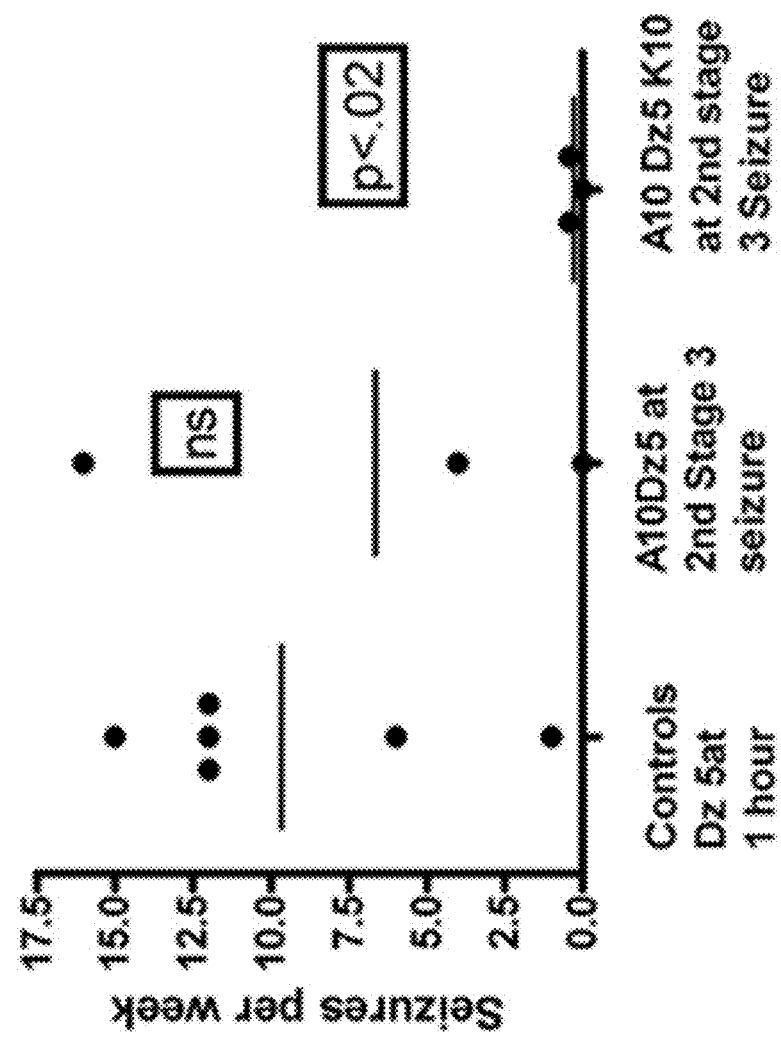
FIG. 6 is a graph examining the effect of dual treatment with a GABAA receptor agonist and an NMDA antagonist on epileptogenesis. In the Tetz model of SE in Wistar rats, frequency of spontaneous recurrent seizures (a measure of epileptogenesis) was measured 6-8 weeks after treatment. Diazepam (5 mg/kg) did not reduce seizure frequency compared to controls not receiving anticonvulsants. However, when a GABAA receptor agonist (diazepam) was combined with an NMDA antagonist (ketamine), seizure frequency was reduced.

In the Tetz model of SE in Wistar rats, the frequency of spontaneous recurrent seizures (a measure of epileptogenesis) was measured 6-8 weeks after treatment. Diazepam (5 mg/kg) did not reduce seizure frequency compared to controls not receiving anticonvulsants. However, when a GABAA receptor agonist (diazepam) was combined with an NMDA antagonist (ketamine), seizure frequency was reduced (FIG. 6).

Although not wishing to be bound by any particular theory, these results suggest that polytherapy can be more effective and less toxic than monotherapy in the treatment of SE, and that therapy for SE and acute seizures may be based on different principles than that of chronic epilepsy.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A composition comprising at least one GABAA receptor agonist, at least one NMDA antagonist, and at least one additional therapeutic for the treatment or amelioration of nerve agent poisoning;
wherein the at least one GABAA receptor agonist is a benzodiazepine;
wherein the at least one NMDA antagonist is ketamine; and
wherein the at least one additional therapeutic is selected from the group consisting of an anticonvulsant and an antiepileptic.

2. The composition of claim 1, wherein the at least one GABAA receptor agonist is diazepam.

3. The composition of claim 1, wherein the at least one GABAA receptor agonist is midazolam.

4. The composition of claim 1, wherein the at least one anticonvulsant is valproate.

5. The composition of claim 1, wherein the at least one anticonvulsant is brivaracetam.

6. A composition comprising at least one GABAA receptor agonist, at least one NMDA antagonist, and at least one additional therapeutic for the treatment or amelioration of a seizure induced by a disease or disorder;
wherein the at least one GABAA receptor agonist is a benzodiazepine;
wherein the at least one NMDA antagonist is ketamine; and
wherein the at least one additional therapeutic is selected from the group consisting of an anticonvulsant and an antiepileptic.

7. The composition of claim 6, wherein the disease or disorder is selected from the group consisting of an acute seizure, status epilepticus (SE), epilepsy, stroke, traumatic brain injury, and cardiac arrest, drug use, drug withdrawal, alcohol withdrawal, a bacterial, fungal, or viral infection, a tumor, a metabolic encephalopathy associated with hypo- or hyperglycemia, hypo- or hypernatremia, acidosis, alkalosis, hepatic, uremic hypoxic-ischemic or other encephalopathy, an autoimmune or inflammatory process, adegenerative brain disease, and a gene defect.

8. The composition of claim 6, wherein the at least one GABAA receptor agonist is diazepam.

9. The composition of claim 6, wherein the at least one GABAA receptor agonist is midazolam.

10. The composition of claim 6, wherein the at least one anticonvulsant is valproate.

11. The composition of claim 6, wherein the at least one anticonvulsant is brivaracetam.

12. A kit comprising a composition comprising a therapeutically effective amount of at least one GABAA receptor agonist, at least one NMDA antagonist, and at least one additional therapeutic;
wherein the at least one GABAA receptor agonist is a benzodiazepine;
wherein the at least one NMDA antagonist is ketamine; and
wherein the at least one additional therapeutic is selected from the group consisting of an anticonvulsant and an antiepileptic.

13. The kit of claim 12, wherein the kit further comprises a device for administrating the composition.

14. The kit of claim 13, wherein the device is an autoinjector.

15. The composition of claim 1, wherein the at least one GABAA receptor agonist is a benzodiazepine selected from the group consisting of diazepam, and midazolam, and the at least one additional therapeutic is selected from the group consisting of valproate and brivaracetam.

16. The composition of claim 6, wherein the at least one GABAA receptor agonist is a benzodiazepine selected from the group consisting of diazepam, and midazolam, and the at least one additional therapeutic is selected from the group consisting of valproate and brivaracetam.

17. The kit of claim 12, wherein the at least one GABAA receptor agonist is a benzodiazepine selected from the group consisting of diazepam, and midazolam, and the at least one additional therapeutic is selected from the group consisting of valproate and brivaracetam.

* * * * *